США009052371B1

United States Patent
Aposotolos et al.

(10) Patent No.: US 9,052,371 B1
(45) Date of Patent: Jun. 9, 2015

(54) COMBINATIONAL NUCLEAR QUADRUPOLE RESONANCE (NQR) AND NUCLEAR MAGNETIC RESONANCE (NMR) APPARATUS WITH LINEAR FREQUENCY CHIRP DETECTED SIGNALS

(71) Applicant: AMI Research & Development, LLC, Windham, NH (US)

(72) Inventors: John T. Apostolos, Lyndeborough, NH (US); Judy Feng, Nashua, NH (US); William Mouyos, Windham, NH (US)

(73) Assignee: AMI Research & Development, LLC, Windham, NH (US)

( * ) Notice: Subject to any disclaimer, the term of this patent is extended or adjusted under 35 U.S.C. 154(b) by 0 days.

(21) Appl. No.: 14/263,226

(22) Filed: Apr. 28, 2014

Related U.S. Application Data

(60) Provisional application No. 61/816,866, filed on Apr. 29, 2013.

(51) Int. Cl.
*G01R 33/44* (2006.01)
*G01R 33/48* (2006.01)

(52) U.S. Cl.
CPC .......... *G01R 33/441* (2013.01); *G01R 33/4808* (2013.01)

(58) Field of Classification Search
USPC .......................... 324/300–322; 600/407–435; 382/115–132; 702/23; 342/22; 250/291
See application file for complete search history.

(56) References Cited

U.S. PATENT DOCUMENTS

| 4,959,543 | A | * | 9/1990 | McIver, Jr. et al. | 250/291 |
|---|---|---|---|---|---|
| 5,814,987 | A | * | 9/1998 | Smith et al. | 324/300 |
| 6,091,356 | A | * | 7/2000 | Sanders et al. | 342/132 |
| 6,522,135 | B2 | | 2/2003 | Garroway et al. | |
| 6,777,937 | B1 | | 8/2004 | Miller et al. | |
| 6,822,444 | B2 | | 11/2004 | Lai | |
| 7,187,169 | B2 | | 3/2007 | Clarke et al. | |
| 7,307,781 | B1 | * | 12/2007 | Chang et al. | 359/326 |
| 7,403,006 | B2 | * | 7/2008 | Garwood et al. | 324/310 |
| 7,425,828 | B2 | * | 9/2008 | Garwood et al. | 324/310 |
| 7,471,224 | B2 | * | 12/2008 | Babbitt et al. | 341/133 |

(Continued)

FOREIGN PATENT DOCUMENTS

WO     WO 2013049270 A1 * 4/2013

OTHER PUBLICATIONS

Augustine et al., "Squid detected NMR and NQR," Solid State Nuclear Resonance 11 (1998) p. 139-156.
Espy et al., "Ultra-low-field MRI for the detection of liquid explosives," Superconductor Science and Technology, 23 (2010) 034023 (8 pages), Feb. 22, 2010.

(Continued)

*Primary Examiner* — Melissa Koval
*Assistant Examiner* — Tiffany Fetzner
(74) *Attorney, Agent, or Firm* — Cesari and McKenna, LLP

(57) ABSTRACT

A structure or method for detecting a substance using conductive surfaces. Segments of conductive wire are disposed adjacent each of the surfaces and multi-turn coils are also disposed between the two surfaces, typically such that the windings of the coils are disposed between the respective conductive wires and the surfaces. A linear chirp signal, is applied to the wire segments. With the coils deactivated, emissions from the wire induce the Nuclear Quadrupole Resonance (NQR). With the coils activated to generate a static magnetic field, emissions from the wire induce Nuclear Magnetic Resonance (NMR). As a result, the characteristics of a substance located between the conductive surfaces may be determined using either or both resonant modalties.

11 Claims, 4 Drawing Sheets

(56) References Cited

U.S. PATENT DOCUMENTS

| | | | |
|---|---|---|---|
| 7,623,908 B2* | 11/2009 | Boppart et al. | 600/477 |
| 7,777,484 B2* | 8/2010 | Garwood et al. | 324/307 |
| 7,973,697 B2* | 7/2011 | Reilly et al. | 342/22 |
| 7,973,936 B2* | 7/2011 | Dantus | 356/451 |
| 8,067,936 B2* | 11/2011 | Garwood et al. | 324/307 |
| 8,300,669 B2* | 10/2012 | Dantus et al. | 372/25 |
| 8,519,707 B2* | 8/2013 | Corum et al. | 324/307 |
| 8,660,803 B2* | 2/2014 | Apostolos et al. | 702/23 |
| 2007/0188171 A1* | 8/2007 | Garwood et al. | 324/310 |
| 2007/0188172 A1* | 8/2007 | Garwood et al. | 324/310 |
| 2007/0211922 A1* | 9/2007 | Crowley et al. | 382/115 |
| 2009/0027050 A1* | 1/2009 | Garwood et al. | 324/307 |
| 2009/0136104 A1 | 5/2009 | Hajian et al. | |
| 2009/0264733 A1* | 10/2009 | Corum et al. | 600/420 |
| 2010/0253340 A1* | 10/2010 | Corum et al. | 324/309 |
| 2010/0253341 A1* | 10/2010 | Corum et al. | 324/309 |
| 2010/0315082 A1* | 12/2010 | Garwood et al. | 324/307 |
| 2012/0092010 A1* | 4/2012 | Corum et al. | 324/309 |
| 2013/0116932 A1* | 5/2013 | Apostolos et al. | 702/23 |
| 2013/0300412 A1* | 11/2013 | Apostolos et al. | 324/309 |
| 2013/0320980 A1* | 12/2013 | Corum et al. | 324/314 |
| 2014/0210464 A1* | 7/2014 | Apostolos et al. | 324/307 |

OTHER PUBLICATIONS

Fan et al., "Low-frequency nuclear magnetic resonance and nuclear quadrupole resonance spectrometer based on a dc superconducting quantum interference device," American Institute of Physics, Rev. Sci. Instrum. 62 (6) Jun. 1991, p. 1453-1459.

Erik Gudmundson, "Signal Processing for Spectroscopic Applications," Acta Universitatis Upsaliensis, *Uppsala Dissertations from the Faculty of Science and Technology* 91, 192 pages. Uppsala, 2010.

R.E. de Souza et al, "NMR and MRI Obtained with High Transition Temperature DC SQUIDs," Journal of the Brazilian Chemical Society, vol. 10, No. 4, San Paulo, Brazil, Jul./Aug. 1999, 12 pages.

TonThat et al., "Direct current superconducting quantum interference device spectrometer for pulsed nuclear magnetic resonance and nuclear quadrupole resonance at frequencies up to 5 MHz," American Institute of Physics, Rev. Sci. Instrum. 67 (8), Aug. 1996, pp. 2890-2893.

Wang et al, "Ultra-Low-Field MRI and Spin-Lattice Relaxation Time of $^1$H in the Presense of $Fe_3O_4$ Magnetic Nano-Particles Detected With a High-$T_c$ DC-Squid,"IEEE Transactions of Applied SuperConductivity, vol. 23, No. 3, Jun. 2013, 4 pages.

Helmholtz Coil, from Wikipedia, the free encyclopedia, http://en.wikipedia.org/wiki/Helmhollz_coil, last modified Mar. 9, 2014, 4 pages.

* cited by examiner

COMBINATIONAL NUCLEAR QUADRUPOLE RESONANCE (NQR) AND NUCLEAR MAGNETIC RESONANCE (NMR) APPARATUS WITH LINEAR FREQUENCY CHIRP DETECTED SIGNALS

CROSS REFERENCE TO RELATED APPLICATIONS

This application claims priority to a U.S. Provisional Patent Application entitled "MRI/NMR Enhanced NQR System", Ser. No. 61/816,866 filed Apr. 29, 2013, the entire contents of which are hereby incorporated by reference.

BACKGROUND

1. Technical Field

This application relates to a detecting liquid and solid substances through the use of very low power applied electromagnetic fields, and more particularly to an apparatus and method suitable for both detecting the same through both Nuclear Magnetic Resonance (NMR) and Nuclear Quadrupole Resonance (NQR).

2. Background

Various "spectroscopic" techniques are used to measure a variety of different atomic and molecular properties (concentration, amount, type, molecular structure, and much more) through an instrument that gives a signal response as a function of frequency (or energy); i.e., an instrument that gives a spectrum. Examples of such techniques include Raman absorption, and Mossbauer spectroscopy, nuclear magnetic resonance (NMR), magnetic resonance imaging (MRI), and nuclear quadrupole resonance (NQR).

NMR, MRI and NQR all rely on the same general principle, that is, a nuclear resonance triggered by the use of radio frequency (RF) pulses. However, NQR differs from NMR and MRI as it does not require an external magnetic field; the nuclear spin states arise from the interaction between the nuclear charge density and the electric field gradient (EFG) at the nucleus, caused by neighboring charges.

To produce nuclear magnetic resonance (NMR) signals, large and powerful magnets are typically needed. Moreover, the stronger the magnetic field, the stronger the received signal and the more detailed the obtained information.

NQR is a solid-state RF spectroscopic technique able to detect compounds with quadrupolar nuclei, i.e., with spin quantum number $I>\frac{1}{2}$ ("spin $\frac{1}{2}$ particles"). Around half of the elements of the periodic table has this property. As opposed to NMR and MRI, no external magnetic field is required for NQR, allowing for portable instruments. However, since the nuclei are not aligned, the signals are very weak.

For more details of the theory behind NMR and NQR detection, see Gudmundson, E., "Signal Processing for Spectroscopic Applications", Department of Information Technology, Uppsala University, SE-751 05, Uppsala, Sweden, © 2010.

Multinuclear NMR/MRI spectroscopy is the name given to the study of NMR active nuclei of elements other than hydrogen 1 (proton) or carbon 13. A wide range of elements with NMR frequencies ranging from silver (18.62 MHz) to Phosphorus (161.98 MHz) can be utilized to detect chemical compounds of interest. Hydrogen is the most frequently imaged nucleus because it is present in biological tissues in great abundance. Any nucleus with a net nuclear spin can potentially be imaged or detected by MRI/NMR. Sodium 23 and Phosphorus 31 are naturally abundant in the human body and could be imaged or detected directly.

As mentioned above, NMR requires large static magnetic fields, typically ranging from 500 Gauss to 20,000 Gauss to create Zeeman splitting of the original nuclei state. A high power RF pulse is used to excite nuclei from the lower state to the higher energy state. The excited nuclei fall back to the ground state causing free induction decay which is observed as a weak decaying pulse with oscillations at the Larmor frequency.

In nuclear quadrupole resonance (NQR) the splitting of the original nuclei state is caused by the electric fields from the surrounding electron cloud of the atom. Many current NQR systems utilize a high power RF pulse which is used to excite nuclei from the lower state to the higher energy state. Similar to NMR, the excited nuclei fall back to the ground state causing free induction decay which is detected as a decaying RF pulse.

Some have proposed the use of Superconducting Quantum Interference Devices (SQUIDs) as a sensitive detector of magnetic flux for both NMR and NQR spectroscopy. See for example, Augustine, M. P. et al "SQUID Detected NMR and NQR", in *Solid State Nuclear Magnetic Resonance*, Vol 11 (1998) pp. 139-156. SQUIDs introduce a number of complexities, not the least of which is the need for cryogenic cooling to operate them; the resulting SQUID structures are different for the NQR and NMR detection modalities.

SUMMARY

The basic idea here is to provide a structure or method for detecting a substance using two or more conductive surfaces, preferably arranged in parallel and spaced apart from one another. One or more segments of conductive wire are disposed adjacent each of the surfaces, within the space between the two surfaces. Two sets of multi-turn coils are furthermore also disposed between the two surfaces, typically such that the windings of each coil are disposed between one of the conductive wires and one of the surfaces. The coils may be arranged as a Hemholtz coil pair.

A suitable continuous=excitation signal, such as a linear continuous chirp signal, is applied to the wire segments in various modes to determine the characteristics of a substance located between the conductive surfaces.

In a first mode, with the coils deactivated, emissions from the wire segments at certain frequencies induce the Nuclear Quadrupole Resonance (NQR) effect in any substance disposed between the two conductive surfaces.

In a second mode, with the coils activated to generate a static magnetic field, emissions from the wire segments at certain frequencies induce a Nuclear Magnetic Resonance (NMR) effect in any substance located between the two conductive surfaces.

The result increases the sensitivity of known NMR and/or corresponding Magnetic Resonance Imaging (MRI) systems and enable the use of multinuclear NMR/MRI spectroscopy to detect a wide range of substances of interest not otherwise possible with NQR techniques alone.

In more particular aspects, the coils may be embedded in a portal defined by at least four conductive surfaces, such as along the two parallel sides, the top and the floor. A low current is sent through the coils to excite a low energy (approximately 20 Gauss) field inside the portal (compared to as much as 20,000 Gauss in traditional MRI systems).

Since the emitted signal is a continuous chirp incident on the portal contents; the detection processing can detect the coherent energy of the resulting response using chirp matched filters or other techniques. Therefore, chirp signal emission and detection techniques previously known for NQR detection are thus now applied as well for NMR/MRI detection. In the NMR/MRI mode, the emitted chirp signal frequencies may range to as low as only about 100 kHz (as opposed to for example, seeing the effect at 64 Mhz for protons of hydrogen in traditional MRI systems). Since 100 kHz is well within the range of NQR system detection methodologies, the same processing techniques used for NQR and be used in the NMR/MRI mode The applications for this enhanced system may include liquid explosives detection, advanced body imaging, contaminated food detection; functional imaging of the brain and inexpensive MRI machines requiring smaller magnetic fields than current MRI machines.

DETAILED DESCRIPTION OF AN EMBODIMENT

As described below, we have realized that a portal structure and corresponding transmitter and detection processing originally adapted for detecting the presence of substances using the nuclear quadrupole resonance (NQR) effect can be adapted for also inducing and observice a nuclear magnetic resonance (NMR) effect.

Taking nitrogen as one NQR sensitive material of interest, we have realized that the quadrupole resonances of a bound nitrogen nucleus can be well described as a set of three quantum mechanical two-state systems, each with its own resonance frequency. The distortion of the electron cloud of the nitrogen atom by the binding process leads to electric field gradients at the nitrogen nucleus. These gradients enable the quadrupole interaction. Quantum mechanical two-state systems are ultimately governed by the same underlying differential equation. Because the nitrogen nucleus near any of its three resonant frequencies is effectively a polarized quantum mechanical two-state spin system (polarized by the quadrupole interaction energy), its behavior bears a strong resemblance to that of any other two-state spin system polarized by some interaction energy.

A very simple quantum mechanical two-state spin system is a spin ½ particle possessing a magnetic moment and polarized by a magnetic field. This system is relatively easy to analyze as it has a very simple classical analogue which has exactly the same solution as a rigorous quantum mechanical treatment. Consideration of the behavior of the spin ½ polarized particle with the same treatment has led us to realize that an NMR system model may be used as a reasonable proxy for an NQR system, as vice versa, with corresponding scaling of the applied electromagnetic fields and expected response frequencies.

1. Portal Design and Chirp Signal Generation

Figure 1:
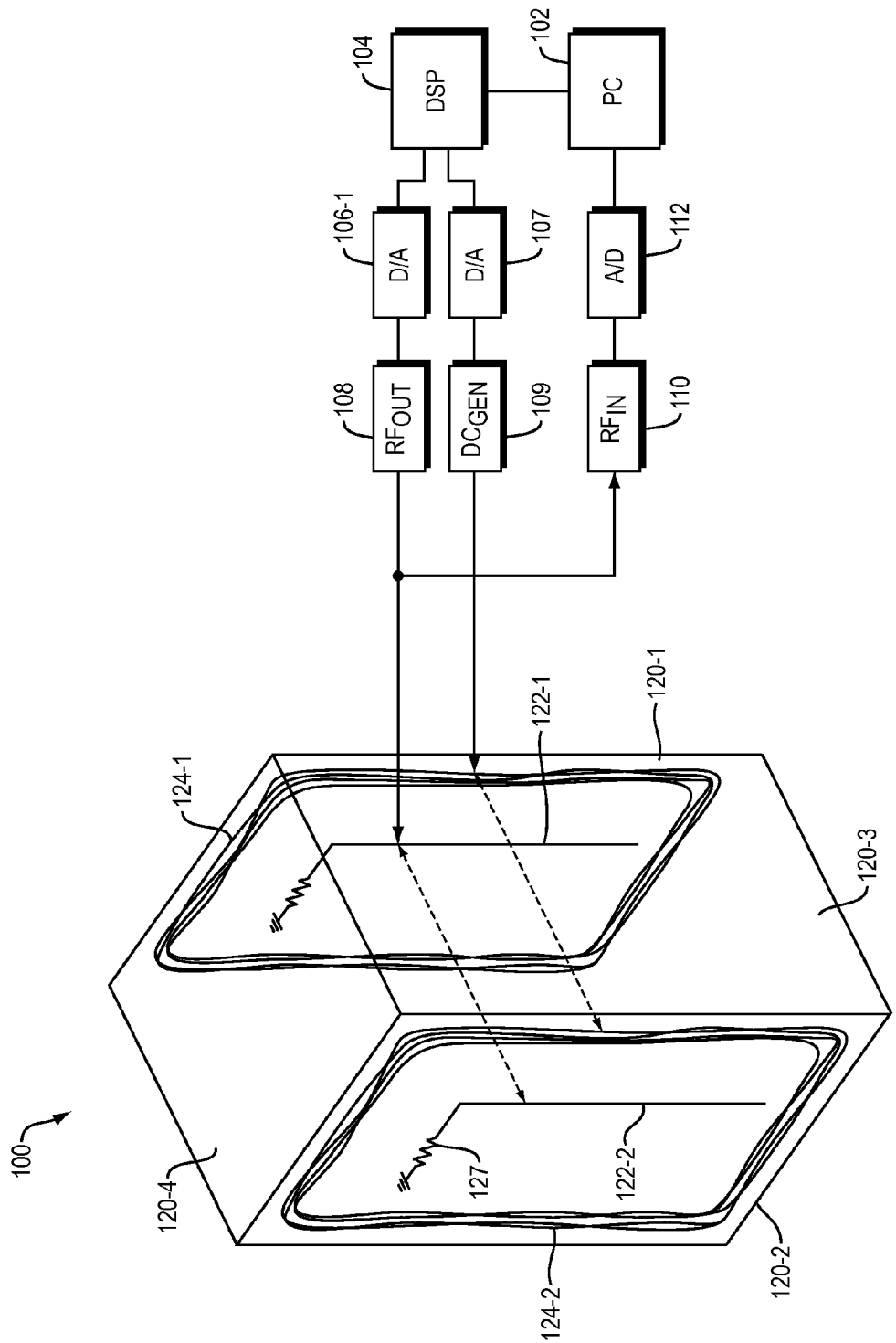
FIG. 1 is an isometric view of a portal and a high level system block diagram.

FIG. 1 is a high-level diagram of the components of a combined Nuclear Quadrupole Resonance (NQR) and Nuclear Quadrupole Resonance (NMR)/Magnetic Resonance Imaging (MRI)-based material detection system according to the teachings herein.

In general, the system may include a portal 100 into which materials of interest are placed. Here the portal 100 consists of four walls 120-1, 120-2, 120-3, 120-4 arranged as right side, left side, bottom and top. At a minimum, the inner surfaces of the walls 120 are formed of or coated with a conductive material, although the walls may be a solid metal such as aluminum as well.

A programmable data processor such as a personal computer (PC) 102 controls a radio frequency (RF) chirp transmitter 108, direct current (DC) generator (DC current fsource) 109, Digital Signal Processor 104 and other circuits such as filters (not shown in FIG. 1) and D/A converters 106, 107 to generate various emission control signals. The generated signals are coupled to transmission line(s) or other conductors disposed within the portal walls to cause electromagnetic fields to be generated within the portal. Receiver circuitry 110 detects an NQR and/or NMR response of a material disposed within the portal. The system then digitizes the response signals with one or more A/D converters 112 and forwards the detected response to the PC 102 typically after further processing by a Digital Signal Processor (DSP) 104. The DSP 104 and/or PC 102 then make a decision as to whether there are certain types of materials in the portal, and displays the result.

Although specific configuration details will vary, the personal computer (PC) 102 may have the typical central processing unit (CPU), memory, disk and/or other mass storage devices, and a display (not shown). The PC 102 stores and executes software programs that implement the functions described herein. A power supply (not shown) provides power to the PC 102 as well as to the other components of the system. An input/output (I/O) subsystem, which may be a peripheral board plugged into the PC via an suitable interface includes a number of digital to analog converters and analog to digital converters.

In addition, the PC may itself include one or more Digital Signal Processor (DSP) hardware chips and/or software platforms to implement transmit signal generation and receive signal detection functions.

In the transmit direction, the PC 102 controls the DSP 104 and/or D/A 106, to generate desired chip signals that include one or more NQR and NMR frequencies of interest. More particularly, each of many RF signals may include a linear chirp signal, for example, a sinusoidal signal having an instantaneous frequency that changes linearly with time. The instantaneous frequency of each chirp signal may be mathematically represented as $$\omega_{instantaneous} = 2\pi F_{start} + 2\pi \left(\frac{BW}{T}\right)t$$

where $F_{start}$ is an initial frequency, BW is a bandwidth (frequency range in hertz) of the chirp, and T is the duration of the chirp.

In one implementation here for an NQR mode, the chirp signal generated by RF transmitter 108 may have a BW of 40 kHz and T may be 1 second.

In one implementation for an NMR mode, the chirp signal generated by RF transmitter 108 may have a BW of 100 kHz and T may be 2 seconds.

The chirp signals preferably originate as digital signal data computed and/or stored by the PC 102. Each digital chirp signal, associated with one or more NQR or NMR frequencies of interest, is fed to the D/A 106, is low-passed filtered, and amplified. As explained in more detail below, multiple analog chirp waveforms with alternating power state illuminations may be generated at a given instant in time via multiple D/As, filters, and amplifiers operating in parallel in the Radio Frequency Output (RFout) circuits 108.

The electromagnetic field(s) generated in response to the chirped RF signals are then made incident on whatever substance is contained in the portal 100, causing coherent radio frequency emissions from the contents. The response signal(s) from the portal contain the transmitted energy, reflected energy, and the chirp signal(s) and are further processed in an NQR mode to determine the presence of materials exhibiting a nuclear quadrupole resonance.

As will be described in more detail below, the DC generator 109 may be selectively enabled with the RF generator 108 to send a current to coil pair 124-1, 124-2 to operate the portal in an NMR mode. In this mode, nuclear magnetic resonance is detected using the same transmitted chirp signal, reflected energy detection, are receiver processing as for the NQR mode.

Signals returned from the portal 100 at receiver 110 are fed to corresponding circuits and A/D converters 112 to provide digital response signals back to the DSP 104 and/or PC 102 for signal processing. The receiver processing may include down conversion, demodulation (dechirping), matched filtering, and other detection processing.

More details of the signal generation, detection and processing, as well as alternative system architectures and components are also described in U.S. patent applications such as Ser. No. 14/132,434 filed Dec. 18, 2013 entitled "Low Power Stimulated Emission Nuclear Quadrupole Resonance with Nonlinearity Corrections and/or With Consideration of Three Adjacent Frequency Bands"; Ser. No. 61/868,693 filed Aug. 22, 2013 entitled "Location of Materials on a Person Standing Within an NQR Portal"; Ser. No. 14/206,394 filed Mar. 12, 2014 entitled "Detection Processing for NQR System"; Ser. No. 61/868,668 filed Aug. 22, 2013 entitled "Waveform Sequencing in Multiplexed NQR System"; U.S. patent application Ser. No. 13/628,824 filed Sep. 27, 2012 entitled "NQR Detection from Continuous Rabi Transitions"; pending U.S. patent application Ser. No. 13/871,468 filed Apr. 26, 2013 entitled "Low Power Stimulated Emission Nuclear Quadrupole Resonance Detection at MultiplePower Levels"; and Ser. No. 14/206,394 filed Mar. 12, 2014 entitled "Detection Processing for NQR System". The entire contents of each of these referenced co-pending patent applications are hereby incorporated by reference.

2. Portal Excitation Design

Also of interest in FIG. 1 is the use of two different excitation structures for emitting signals into the portal 100.

Figure 2B:
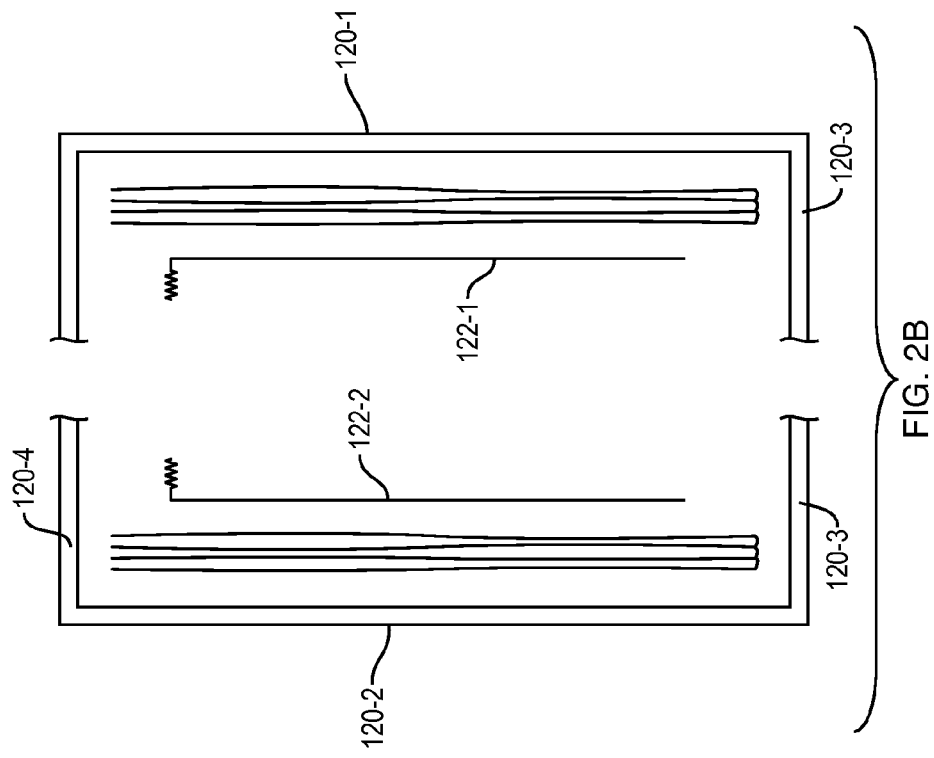
FIG. 2A is an internal plan view and FIG. 2B is a cross sectional view of the portal showing the arrangement of wire segments and coils in more detail.
Figure 2A:
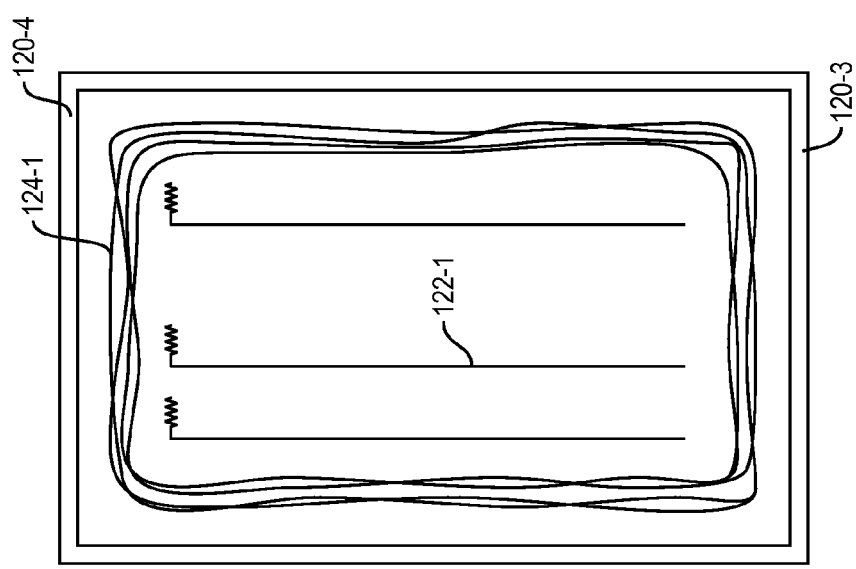

Two or more conductive wires 122-1, 122-2 are a first type of signal emitter, typically disposed within the portal adjacent both a portal right wall 120-1 and left wall 120-2. The conductive wire segments are disposed as straight line wire segments that may be individually terminated via resistors 128 or may be connected together at the roof and arranged as balanced lines (as shown in FIG. 2). The portal top 120-4 and bottom 120-3 walls also act as an RF shield. The wire segments 122 are each located in-board of and spaced apart from a respective one of the side walls 120-1, 120-2. Although only one wire segment is shown adjacent each wall, it is understood that there are typically several such wire segments disposed in parallel along each side wall 120.

Also disposed within the portal is a second type of emitter structure comprising a pair of wire coils 124-1, 124-2. In one example, each coil 124-1, 124-2 has between 100 and 200 turns disposed between a respective one of the walls 120-1, 120-2 and a respective one of the wire segments 122-1, 122-2. The coils may be arranged as an two identical magnetic coils in a configuration known as a Hemholz coil. The turns of the coils 124-1, 124-2 are embedded in fit inside the portal along its sides as seen in FIG. 1. The coils 124-1, 124-2 are energized with a DC signal to generate a static magnetic field in the portal 100 enable an MRI/NMR mode of operation.

In one example for a portal of approximately 8 feet high and 3 feet wide, a current of 10 amps may be sent through each of the coils 124-1, 124-2 to generate a 20 Gauss static field inside the portal 100 for MRI/NMR mode operation. In this mode, the emitted MRI/NMR chirp signal frequency via chirp transmitter 108 will be scaled down to around 100 KHz instead of the 64 MHz signal used in typical prior art NMR/MRI systems. Since 100 kHz is at the bottom range of the co-resident NQR detection system, all the receiver processing methodologies of that NQR system still apply.

In the NQR mode, the detection system described above disables coils 124-1, 124-2 and only activates RF transmitter 108 to emit a continuous incident electromagnetic wave via wires 122 using continuous wave (CW) chirp signals generated by transmitter 108 while at the same time detecting the coherent energy of the resulting Rabi oscillations, also via wires 122. The coherent integration enables detection of a wide range of explosives using relatively low power CW chirp waveforms.

In a similar manner this methodology is applied to operation in an NMR/MRI mode using a low power continuous wave (CW) chirp generated by transmitter 108 but with the coil 124 also energized by DC generator 109. Prior art MRI systems typically use a 15,000 Gauss field to detect hydrogen at a free induction decay frequency of 64 MHz. We instead replace the expensive 15,000 Gauss field with a much lower field and are able to detect the lower frequency Rabi oscillations with the coherent processing the same as that used in the NQR mode.

The result increase the sensitivity of known Magnetic Resonance Imaging (MRI) systems and enable the use of multinuclear NMR/MRI spectroscopy to detect a wide range of substances of interest not otherwise possible with NQR techniques alone.

In addition, the MRI/NMR coils 124-1, 124-2 each have a relatively high inductance, such as 0.125 Henries each. This high coil inductance is preferred so that that the presence of coils 124-1, 124-2 does not adversely affect the operation of the conductors 122 in the NQR mode.

It is also observed that the specific magnetic field strength emitted by the coils 124-1, 124-2 affects the expected resonant frequencies for different materials in the NMR mode. Thus the expected NMR emission frequencies can be changed by changing the DC power level emitted by generator 109. It may be desirable in some implementations to operate the system in a couple of different NMR field strengths to increase the number of materials of interest that can be detected by the system.

3. Transmit and Receive Filtering; Detection Processing

Figure 3:
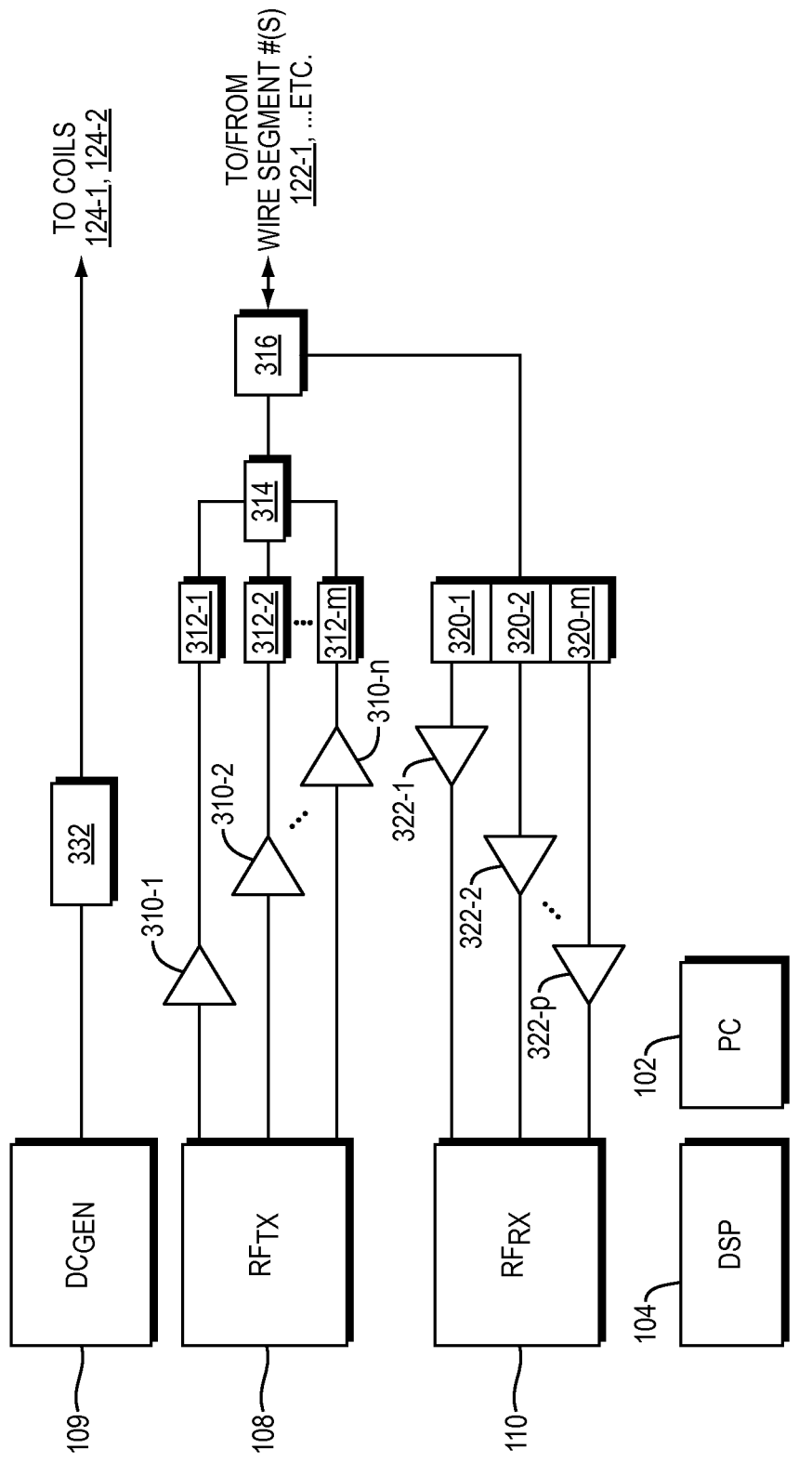
FIG. 3 is a high level schematic of the direct current and chirp signal generation and detection components.

FIG. 3 is a high level diagram of transmitter and receiver analog circuits. Transmitter 108 (RFout) is responsible for generating the linear frequency chirp signals and may include several amplifiers 310-1, 310-2, . . . , 310-$n$, filters 312-1, 312-2, . . . , 312-$m$, reactive combiner/multiplexer(s) 314 and directional coupler 316. The resulting chirp signals are fed to the conductive wire segments 122.

On the receive side, signals picked up by the conductive wire segments 122 are fed through directional coupler 316 to one or more receive filters 320-1, 320-1, . . . , 320-$m$ and amplifiers 322-1, 322-2, . . . , 322-$p$. The exact number and arrangement of filters and amplifiers on both the transmit and receive legs depends on the specific materials of interest, how many resonances are to be excited simultaneously, system cost considerations, and other factors. Several different architectures are described in the co-pending patents and patent applications referenced elsewhere herein.

Also shown in FIG. 3 is the transmit circuitry for DC generator 109 responsible for generating the DC signal to generate the static magnetic field via coils 124-1, 124-2. An amplifier or other current control 332 may control the exact current level applied to the coils 124-1, 124-2 and thus the strength of the resulting static magnetic field in the portal.

Detection processing implemented by the DSP 104 and/or PC 102 can otherwise be as in any of the Nuclear Quadrupole Resonance (NQR) detection system(s) described in the other patents and patent applications referenced elsewhere herein.

4. Selective Control of Static Magnetic Field for NQR/NMR Modes

Figure 4:
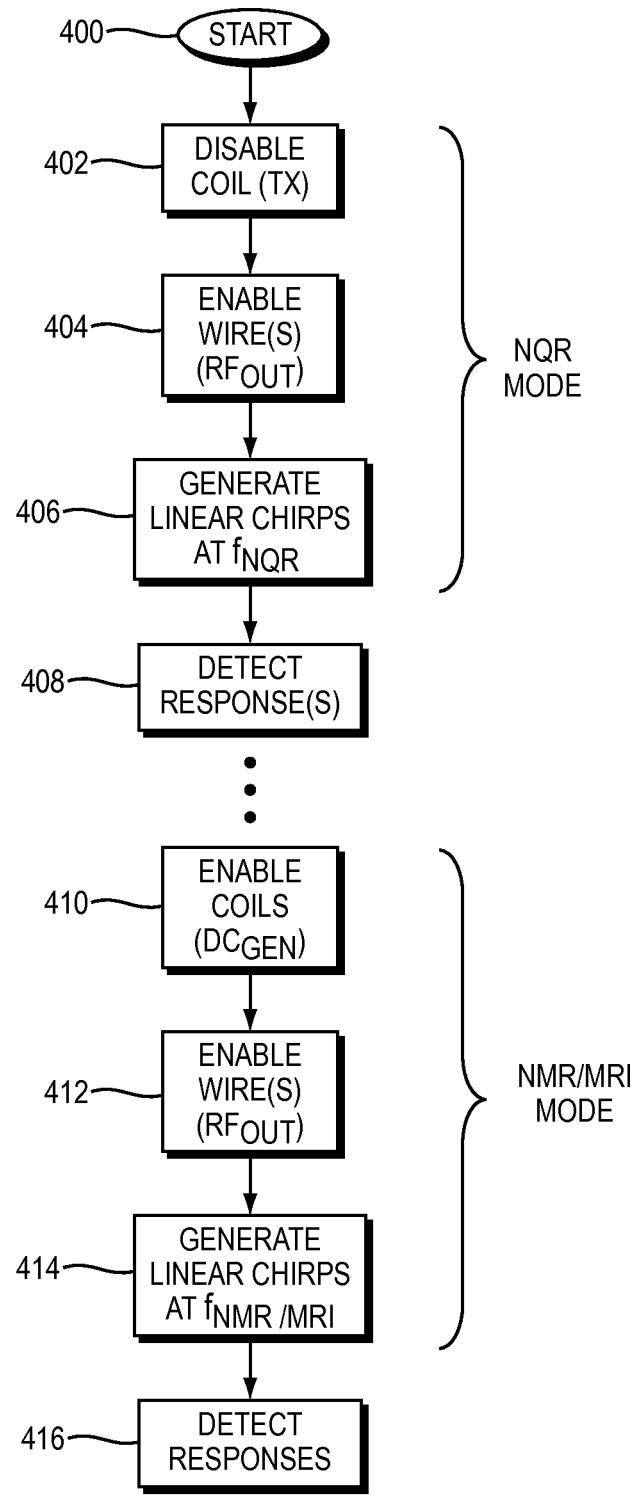
FIG. 4 is a flow diagram for control of the DC generator connected to the coils and RF chirp transmitter connected to the wire segments.

FIG. 4 is an example flow diagram for a control program implemented by the PC 102 to selectively operate the system in either the NQR mode or NMR mode. From an initial state 400, an NQR mode is entered by disabling coil 124 (state 402). Next the RF transmitter TX 108 is enabled (state 404) and chirp waveforms that include NQR frequencies of interest are generated (state 406) and responses detected (state 408). In this state NQR-sensitive materials present in the portal 100, such as may include nitrogen, are determined.

At some other time, the coils 124-1, 124-2 are energized via DC generator 109 (state 410). The RF transmitter 108 is again enabled to couple chirp signals to wire conductors 122 (state 412) but here the chirps generated encompass expected NMR responses of interest (state 414). The responses are detected (state 416) to determine NMR sensitive materials of interest located in the portal.

What is claimed is:

1. A combined Nuclear Quadrupole Resonance (NQR) and Nuclear Magnetic Resonance (NMR) apparatus comprising:
   a first and second conductive surface arranged in parallel with one another;
   a first and second conductive wire segment disposed along and adjacent to a respective one of each of the first and second conductive surfaces;
   a first and second electromagnetic coil each comprising a winding formed as a plurality of wire turns, the first and second coils being disposed between respective ones of the first and second conductive surfaces; and
   a signal transmitter coupling a linear frequency chirped signal to each of the first and second wire segments;
   a direct current (DC) generator selectively coupling to the electromagnetic coils in order to generate a static magnetic field; and
   a controller, which controls the signal transmitter and DC generator in two modes of operation by
   enabling the signal transmitter while disabling the DC generator in an NQR mode of operation and thereby create a time varying electromagnetic field that induces a Nuclear Quadrupole Resonance (NQR) in a substance located adjacent the first and second surfaces;
   enabling the signal transmitter and enabling the DC generator transmitter in an NMR mode of operation and thereby create a time varying electromagnetic field that induces a Nuclear Magnetic Resonance (NMR) in a substance located adjacent the first and second surfaces;
   a receiver receiving the resulting NQR and NMR radio frequency emissions;
   a processor, determining characteristics of the substance from the resulting NQR and NMR radio frequency emissions; and
   a display for displaying said determined characteristics of the substance.

2. The apparatus of claim 1 wherein the wire turns of the first electromagnetic coil are disposed between the first conductive surface and the first wire segment, and wherein the turns of the second electromagnetic coil are disposed between the second conductive surface and the second wire segment.

3. The apparatus of claim 1 wherein the resulting radio frequency emissions are received via at least one of the wire segments.

4. The apparatus of claim 1 wherein the conductive surfaces include at least four conductive surfaces in order to define a portal having a top, bottom, and left and right sides, and two or more wire segments are disposed adjacent each of the left and right side conductive surfaces.

5. The apparatus of claim 1 wherein the linear chirp signal is a continuous linear chirp.

6. The apparatus of claim 5 wherein a frequency range of the linear chirp signal in an NQR mode of operation is different than a frequency range of the linear chirp signal in an NMR mode of operation.

7. The apparatus of claim 1 wherein the generated magnetic field in the NMR mode is in a range of less than 100 gauss.

8. The apparatus of claim 1 wherein a power level of the DC generator determines a frequency range of the NMR mode.

9. The apparatus of claim 1 wherein the first and second wire segments are conductors disposed in a straight line path adjacent respective ones of the first and second conductive surfaces.

10. The apparatus of claim 1 wherein an impedance of each of the electromagnetic coils is sufficiently high in order to not interfere with operation of the receiver.

11. A method of detecting a substance via Nuclear Quadrupole Resonance (NQR) and Nuclear Magnetic Resonance (NMR) comprising:
   a first and second conductive surface arranged in parallel with one another;
   a first and second conductive elongated wire segment disposed along and adjacent to a respective one of each of the first and second conductive surfaces;
   a first and second electromagnetic coil each comprising a winding formed as plurality of wire turns, the first and second coils being disposed between respective ones of the first and second conductive surfaces; and
   coupling a linear frequency chirped signal transmitter to the first and second elongated wire segments;
   coupling a direct current (DC) source to the first and second electromagnetic coils disposed adjacent the elongated wire segments;
   enabling the signal transmitter while disabling the DC source in an NQR mode of operation and thereby creating a time varying electromagnetic field that induces a Nuclear Quadrupole Resonance (NQR) in a substance located adjacent the wire segments and coils;
   enabling the signal transmitter and enabling the DC source in an NMR mode of operation and thereby creating a time varying electromagnetic field that induces a Nuclear Magnetic Resonance (NMR) in a substance located adjacent the wire segments and coils;
   receiving resulting NQR and NMR radio frequency emissions;
   processing the resulting radio frequency emissions;
   determining characteristics of the substance using both NQR and NMR detection processing; and
   displaying the characteristics of the substance.

* * * * *